United States Patent [19]
Okuda et al.

[11] Patent Number: 6,086,616
[45] Date of Patent: Jul. 11, 2000

[54] PROSTHETIC LEG WITH EXTENSION AUXILIARY MECHANISM

[75] Inventors: Masahiko Okuda; Kotaro Tanaka; Kiyoshi Morimoto; Yasukazu Furuichi; Norio Shiraishi, all of Kobe, Japan

[73] Assignee: Nabco Limited, Hyogo-ken, Japan

[21] Appl. No.: 09/271,780

[22] Filed: Mar. 18, 1999

[30] Foreign Application Priority Data

Apr. 3, 1998 [JP] Japan .................................. 10-108591

[51] Int. Cl.[7] ...................................................... A61F 2/64
[52] U.S. Cl. ................................................................ 623/44
[58] Field of Search .................................. 623/39, 44, 46

[56] References Cited

U.S. PATENT DOCUMENTS

| | | |
|---|---|---|
| 4,310,932 | 1/1982 | Nader et al. . |
| 4,911,709 | 3/1990 | Marlow et al. . |
| 5,344,446 | 9/1994 | Sawamura et al. . |
| 5,545,232 | 8/1996 | Van de Veen ............................. 623/44 |
| 5,728,173 | 3/1998 | Chen ......................................... 623/44 |
| 5,746,774 | 5/1998 | Kramer ...................................... 623/44 |
| 5,888,236 | 3/1999 | Van de Veen ............................. 623/44 |
| 5,921,358 | 7/1999 | Gramnäs .................................... 623/44 |

*Primary Examiner*—Michael J. Milano
*Attorney, Agent, or Firm*—Pitney, Hardin, Kipp & Szuch, LLP

[57] ABSTRACT

There is provided a prosthetic leg with an extension auxiliary mechanism 1100 capable of generating an extension torque only when an angle of bending of the knee is small. A knee joint 80 of a thigh prosthesis 170 is of a multi-axis structure, and a front and a rear link 130, 150 together with an upper thigh member 110 and a lower thigh member 120 constitutes a constrained chain. An extension auxiliary mechanism 1100 having a compression spring is supported between the lower thigh member 120 and the rear link 150. An extension torque generated by the extension auxiliary mechanism 1100 is determined by a product of a force caused by biasing of the compression spring and a distance from a line of action of the force to the center of rotation of the rear link 150. Here, at a stage where the bending angle of the knee exceeds, for example, 15 degrees, an axis of the compression spring is brought generally into alignment with a connecting portion 170O between the rear link 150 and the lower thigh member 120. By doing so, the distance related to the extension torque becomes approximately zero and the extension torque itself becomes approximately zero.

14 Claims, 11 Drawing Sheets

PROSTHETIC LEG WITH EXTENSION AUXILIARY MECHANISM

BACKGROUND OF THE INVENTION

This invention relates to a prosthetic leg with a multi-axis knee joint applied with a link mechanism, and more particularly to a multi-axis knee joint having an extension auxiliary mechanism for preventing immediate bending of the knee joint when the prosthetic leg is in its stance phase.

In general, a prosthetic leg with a knee which can be bent and extended, includes an upper thigh member to which a load of a wearer is applied through the thigh, a lower thigh member supporting on its lower end a leg member, and a knee joint for connecting the upper thigh member to the lower thigh member. There are two types of knee joints, one being a single-axis type which has a single rotational axis and the other being a multi-axis type which is applied with a link mechanism. When the knee is bent and extended, the single rotational axis itself in the single-axis knee joint is normally served as the center of rotation. In contrast, in the multi-axis knee joint, the position of the center of rotation (or instantaneous center) is varied in accordance with bend and extension of the knee. This variation in the center of rotation is desirable in respect of providing a natural and beautiful walking style (i.e., walking attitude).

Incidentally, when a prosthetic leg is designed, it is important that a countermeasure is provided to prevent immediate bend of the knee in the stance phase. In this respect, since the single-axis knee joint is comparatively simple in structure, a load brake for generating a braking force when a load of the wearer is incurred to the prosthetic leg, can be disposed around the rotational axis. In contrast, in the multi-axis knee joint, since at least two front and rear links are essentially employed one at the front side of the knee and the other at the rear side of the knee, it is difficult to install a load brake on the knee portion. In the extended state of the knee, however, an instantaneous center, in the multi-axis knee joint, is located at an area near the crotch joint which is situated upwardly of the actual knee portion. For this reason, the person wearing the multi-axis type prosthetic leg can easily maintain a stable state of the knee by a so-called voluntary control operation.

The extension auxiliary mechanism according to the present invention renders a force for extending the knee to such a multi-axis knee joint and it is a mechanism effective for preventing immediate bend of the knee. U.S. Pat. No. 4,310,932 (corresponding to Japanese Patent Examined Publication (Kokoku) No. Sho 61-44504) and U.S. Pat. No. 4,911,709 (corresponding to Japanese Patent Unexamined Publication (Kokai) No. Sho 62-295658) disclose prosthetic legs with an extension auxiliary mechanism using a coiled spring with respect to the multi-axis type prosthetic leg. In those extension auxiliary mechanisms, however, there is provided not only the function for preventing immediate bend of the knee in the stance phase but also the function for assisting bending of the knee joint at a large angle in the swing phase.

In order to control the prosthetic leg with a high degree of precision, it is desirable to be capable of making a control of the leg in the swing phase and making an immediate knee bend prevention control in the stance phase separately or independently. By doing so, a more appropriate control can be made in accordance with a walking speed. The controlling technique itself in the swing phase is well known. For example, U.S. Pat. No. 5,344,446 (corresponding to Japanese Patent No. 2501346) discloses a technique for making a control using an air-cylinder device such that an opening degree of a valve in the cylinder varies in accordance with a walking speed.

The present invention has been accomplished under such a basic technical concept that the prevention of the immediate bend of the knee portion in the stance phase and the control in the swing phase should be made independently.

SUMMARY OF THE INVENTION

It is, therefore, a main object of the present invention to provide a prosthetic leg with an extension auxiliary mechanism capable of generating an extension torque only when a bending angle of the knee is small.

Another object of the present invention is to provide a prosthetic leg capable of independently controlling an extension auxiliary mechanism for preventing immediate bending of the knee and a swing phase control unit capable of making a walking style of its wearer more natural.

A further object of the present invention is to provide a technique most suitable for making a control with a higher degree of precision, using an air-cylinder device as a swing phase control unit.

A knee joint of a prosthetic leg according to the present invention is of a multi-axis structure and includes at least two front and rear links, one being located forwardly of the knee and the other being located backwardly of the knee. When an extension auxiliary structure is chiefly comprised of a spring, its extension torque is determined by a product of a force caused by biasing of the spring and a distance from a line of action of the force to the center of rotation of the links. Thus, it can be contemplated, as means for making the extension torque approximately zero when a bending angle of the knee exceeds a predetermined angle, a method for making the force approximately zero after the bending angle of the knee reaches a predetermined angle or a method for making the distance approximately zero after the bending angle of the knee reaches a predetermined angle. The present invention employs the latter method for making the distance approximately zero. Also, an extension auxiliary mechanism having a spring is disposed in a space between an upper thigh member and a lower thigh member by supporting the extension auxiliary mechanism between the lower thigh member and the rear link. Owing to the foregoing arrangement, it can effectively be avoided that the extension auxiliary mechanism is enlarged in size and the mechanism becomes an obstacle for installing a swing phase control unit.

As the spring of the extension auxiliary mechanism, any of a compression spring and a tension spring can be utilized. An acceptable spring material includes coil, rubber, and the like. Preferably, the spring of the extension auxiliary mechanism is a coiled compression spring. With respect to the compression coiled spring, opposite end portions thereof are each preferably connected to the lower thigh member or the rear link through a spring retainer. By doing so, a thread means for adjusting a spring force or a guide means for guiding biasing of the spring can easily be installed utilizing the spring retainer or a connecting portion.

Referring here to FIGS. 1 and 2 showing one mode of an extension auxiliary mechanism having a compression spring, a basic concept of the present invention will be described. FIG. 1 shows a state in which the knee is completely extended (i.e., a bending angle of the knee is zero) and FIG. 2 shows a state in which the knee is bent maximum in a swing phase (i.e., a bending angle of the knee is 60 degrees, for example). Four links including an upper thigh member 10, a lower thigh member 20, a front link 30 and a rear link 50 constitute a constrained chain. Connecting portions between the adjacent links are mutually rotatably. A connecting portion Q between the front link 30 and the lower thigh member 20 also serves as one connecting portion with respect to a compression spring-attached extension auxiliary mechanism 100. The other connecting portion P of the extension auxiliary mechanism 100 is situated on the rear link 50 but it is offset towards the front link 30 from a straight line which connects two connecting portions B, O together with respect to the upper thigh member 10 and the lower thigh member 20. Therefore, a force F of the compression spring of the extension auxiliary mechanism 100 acts in a direction of a line of action which connects the connecting portions Q, P together. Presuming a distance between the force F and a rotational center O of the rear link 50 is d, an extension torque is determined by a product of the force F and the distance d. As apparent from FIG. 2, in the state in which the knee is bent maximum in a swing phase, the force F has a certain magnitude but the distance d is zero or a value approximately zero. Therefore, the extension auxiliary mechanism 100 generates an extension torque only when the bending angle of the knee is small. For example, when a swing phase control unit such as an air-cylinder or the like is substantially acting, the extension auxiliary mechanism 100 has no effect.

This concept of the present invention exhibits particularly significant effect by being applied to a prosthetic leg having an air-cylinder as a swing phase control unit. The reason is that the air-cylinder device generates a repulsive force after the knee is bent maximum and therefore, such a repulsive force can be utilized for swinging the lower thigh member, but the extension auxiliary mechanism of the present invention generates no extension torque at the stage for generating such a repulsive force. Especially, when a control is made in accordance with a walking speed, a delicate control is needed in case the walking speed is slow, for example. Since the air cylinder device is under no effect of the extension auxiliary mechanism at that time, a control thereof can be made with a high degree of precision. Also, since the extension auxiliary mechanism according to the present invention makes an extension action only at the stage where the bending angle of the knee is small, there can be effectively prevented such an inconvenience that the lower thigh accidentally jumps up when the wearer sits.

The present invention can widely be applied as a technique for preventing bending of the knee in a stance phase to a prosthetic leg with a multi-axis knee joint. For example, it can also be applied to a prosthetic leg having no swing phase control unit and a prosthetic leg having a hydraulic cylinder device as a swing phase control unit. Therefore, when considered as a technique for preventing bending of the knee in a stance phase, an extension action of the extension auxiliary mechanism is available only at an initial stage of bending where the bending angle of the knee is still so small as 0 to 15 degrees.

DETAILED DESCRIPTION OF THE EMBODIMENTS

Figure 1:
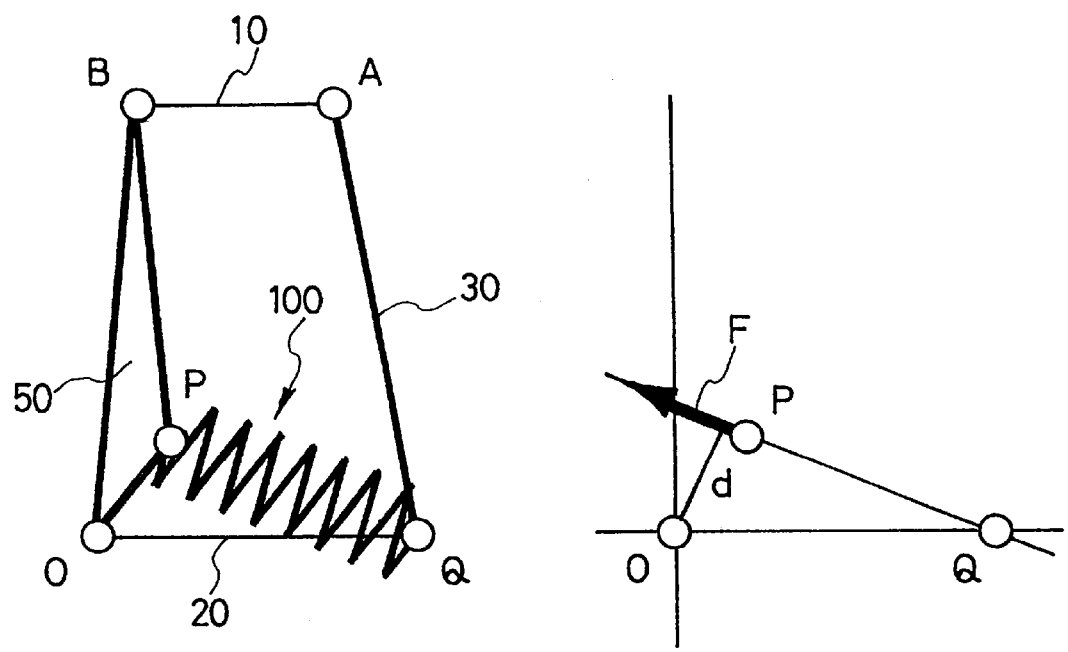
FIG. 1 is a view showing an outline of the present invention and in the illustrated state, the knee is completely extended.
Figure 2:
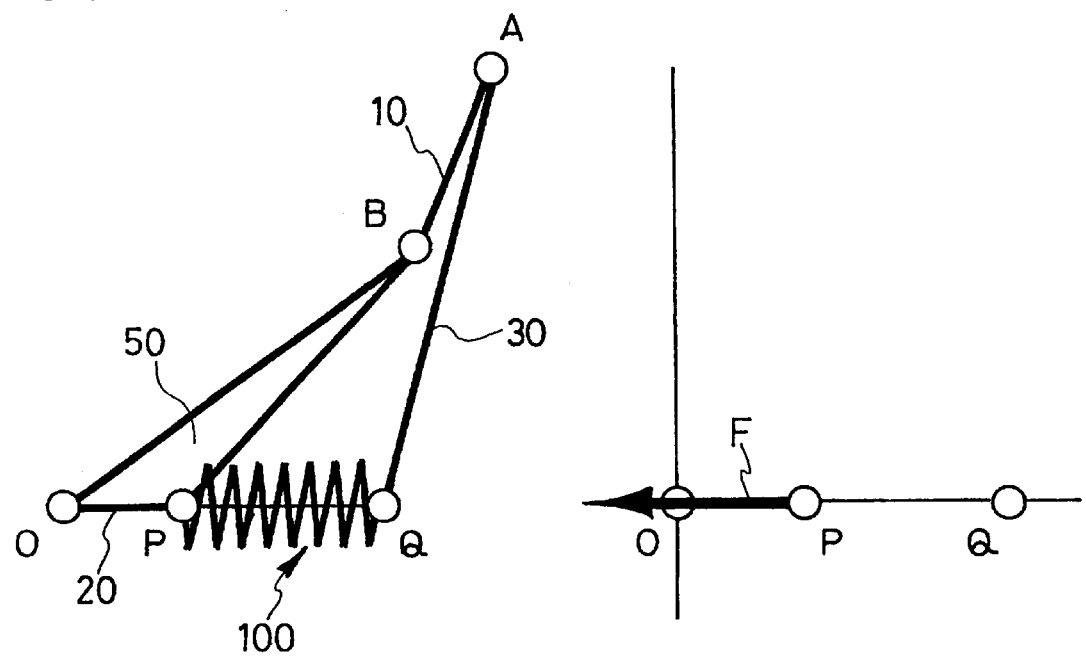
FIG. 2 is a view like FIG. 1 but the knee is bent maximum in a swing phase.
Figure 3:
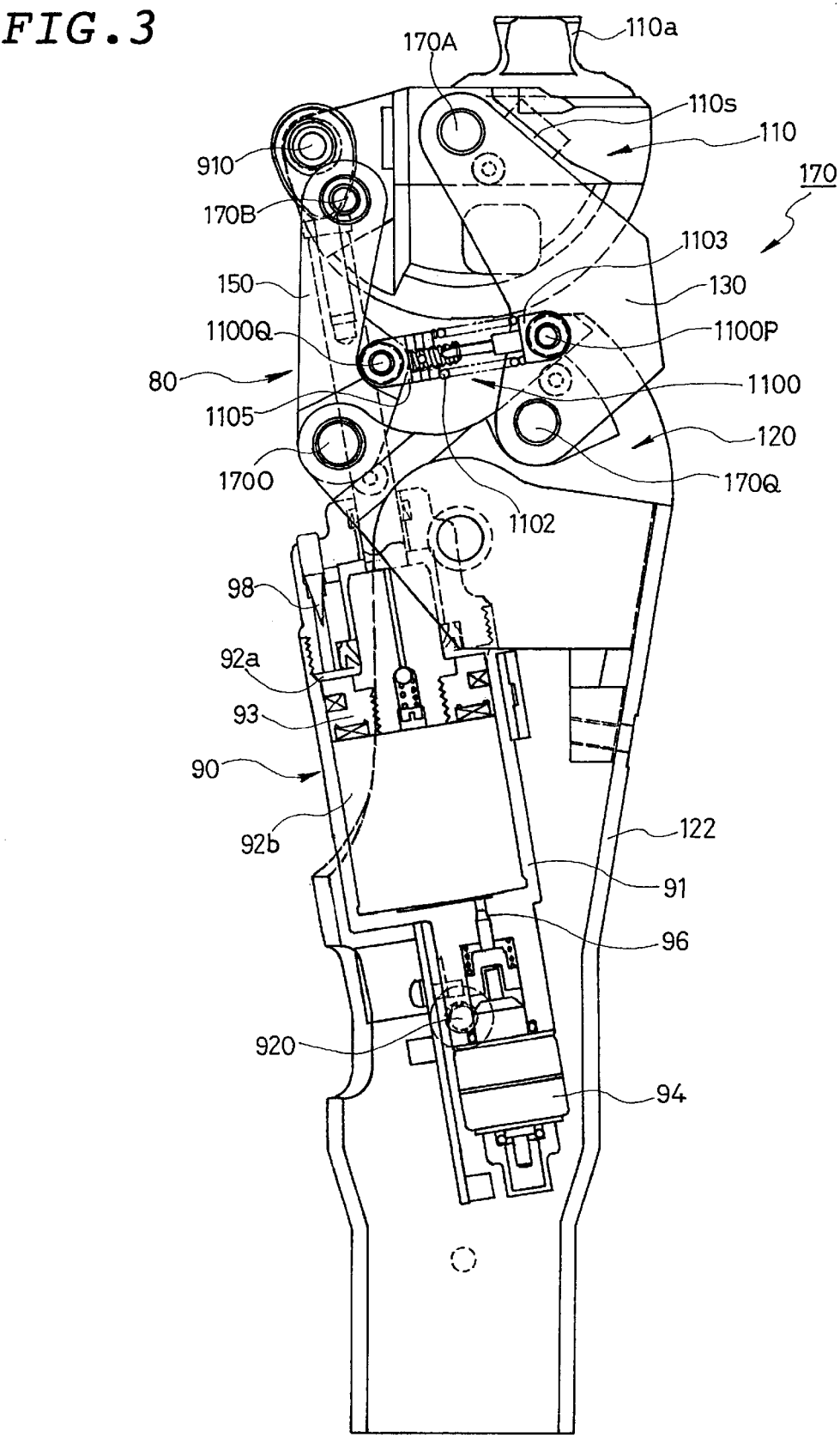
FIG. 3 is a view showing an overall construction of a thigh prosthesis according to the first embodiment of the present invention.

FIG. 3 shows an overall construction of a thigh prosthesis 170 according to the first embodiment of the present invention. There is provided an upper thigh member 110 on an upper portion of the thigh prosthesis 170. The upper thigh member 110 exhibits a shape of the knee. The upper thigh member 110 integrally includes at a part thereof an attachment portion 110a to which a socket, not shown, can be attached. The socket receives therein a cut end to transmit a load of a wearer to the upper thigh member 110 side. On the other hand, there is provided a lower thigh member 120 on a lower portion of the upper thigh member 170. The lower thigh member 120 is chiefly comprised of a hollow frame 122 extending from the knee portion towards the foot. The lower thigh member 120 and the upper thigh member 110 are bendably connected together through a knee joint 80. The thigh prosthesis 170 includes an air-cylinder device 90 as a swing phase control unit. This air-cylinder device 90 is of the same construction as those disclosed in U.S. Pat. No. 5,405,407 and Japanese Patent Unexamined Publication (Kokai) No. Hei 9-551. It includes, among others, a piston 93 for defining a first chamber 92a and a second chamber 92b in a cylinder 91, a variable throttle valve 96 whose degree of opening can be varied in accordance with a walking speed.

Figure 4:
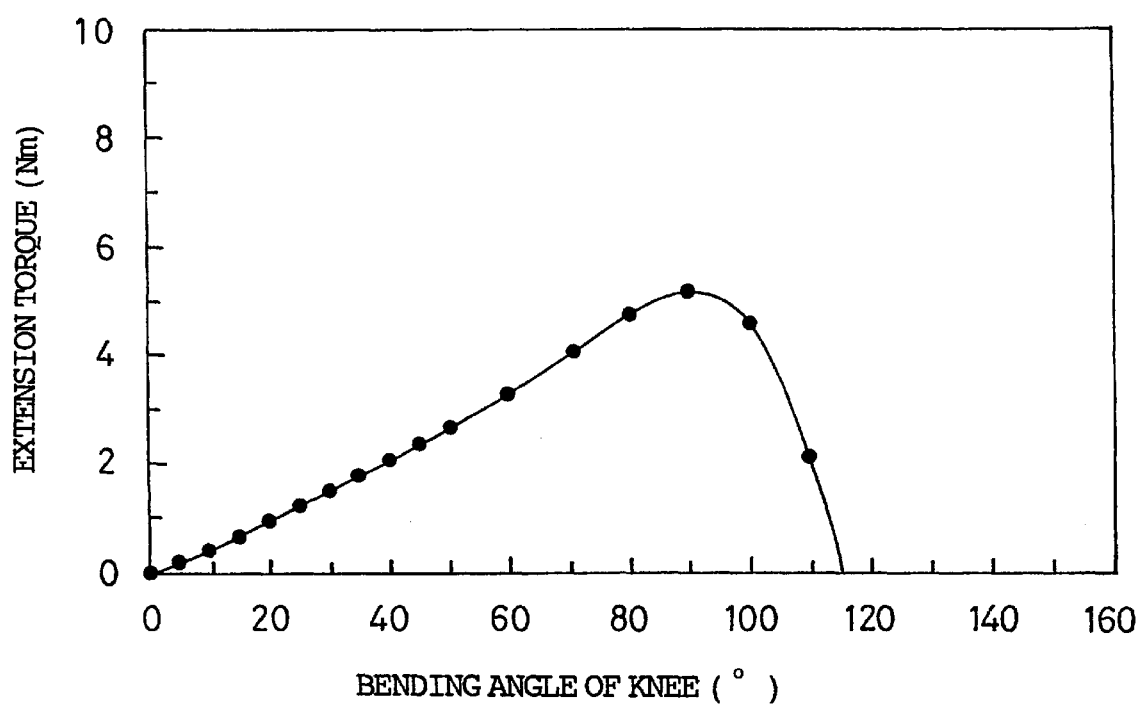
FIG. 4 is a graph showing one characteristic of an air-cylinder device.

Owing to this arrangement, the air-cylinder device 90 can control bending and extension of the knee so as to resemble a natural walk in a swing phase in which the thigh prosthesis 170 leaves from the surface of a floor, etc. FIG. 4 is a graph showing a relation between a bending angle (degree) of the knee when the variable throttle valve 96 is fully open (i.e., in a quick walk) and a repulsive action force (Nm) caused by compression of air. The maximum value of a bending angle of the knee is approximately 60 degrees when the walking speed is in a range from a slow walking to a normal walking, approximately 70 degrees when the walking speed is a quick walking, and approximately 80 degrees when the walking speed is a run with short steps (trot). As shown in FIG. 4, the air-cylinder device 90 generates a substantial action force at a stage where bending of the knee is larger than the maximum bending angle. The air-cylinder device 90 is rotatably supported on both an upper support point 910 on the upper thigh member 110 side and a lower support point 920 on the lower thigh member 120 side.

Figure 5:
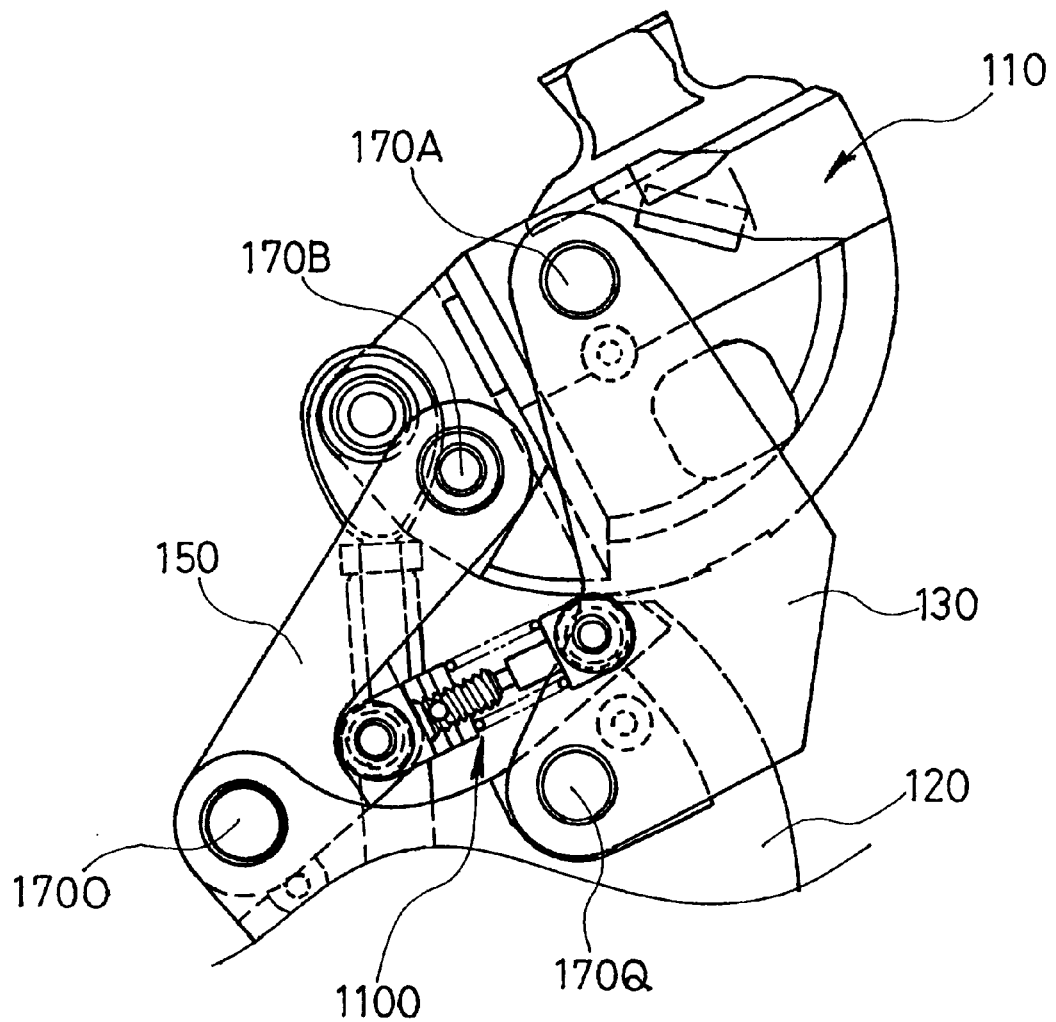
FIG. 5 is a partial view of FIG. 3, but it shows another bending state of the thigh prosthesis.
Figure 6:
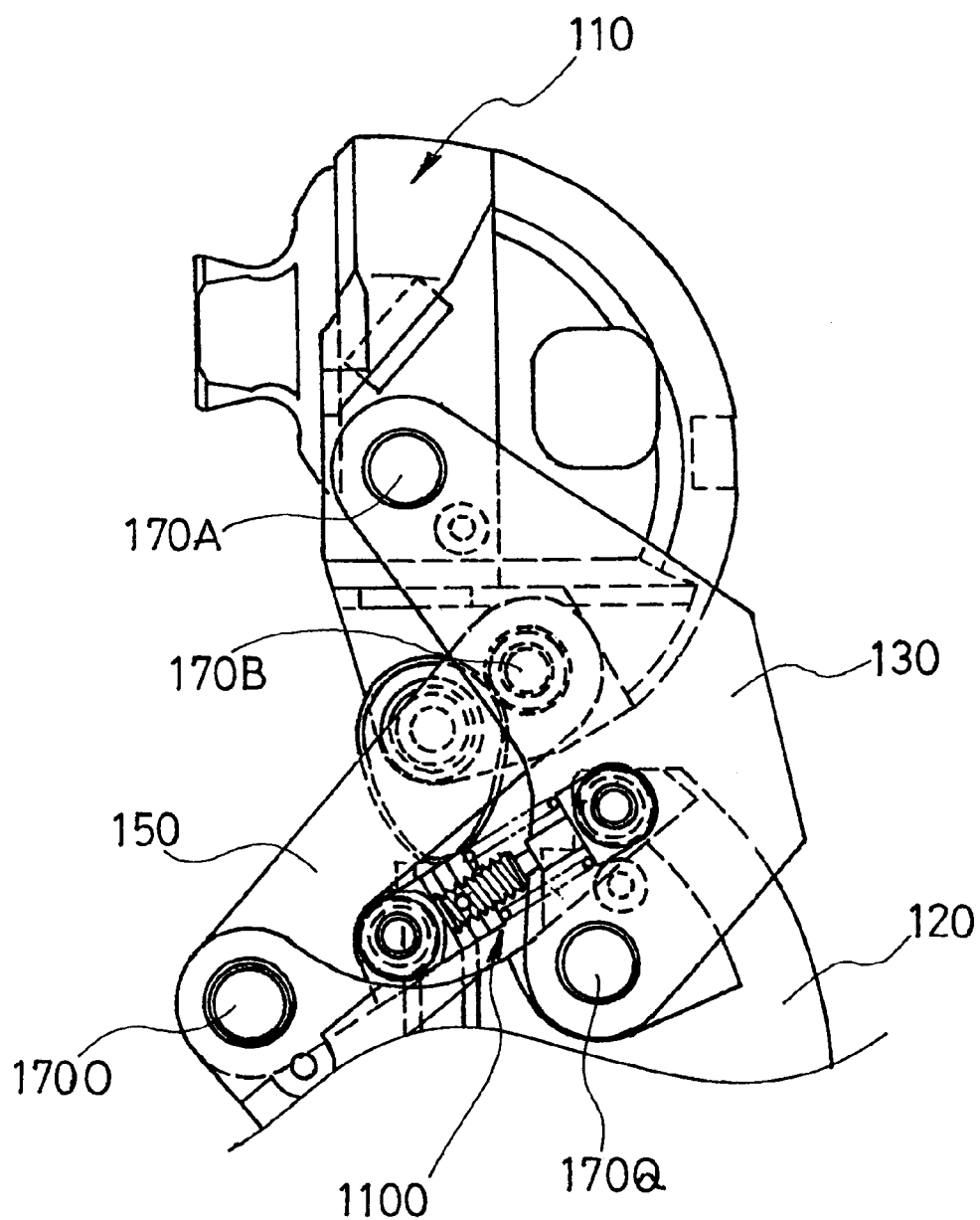
FIG. 6 is a partial view of FIG. 3, but it shows a state in which the thigh prosthesis is bent 90 degrees.

The multi-axis knee joint 80 includes a front link 130 situated forwardly of the knee and a rear link 150 situated backwardly of the knee. When a bending angle of the knee is zero degree, i.e., when the knee is completely extended, the front and rear links 130, 150 are in vertically parallel relation and they are rotatably connected at connecting portions 170A, 170B, 170Q and 170O to the upper thigh member 110 and the lower thigh member 120. By this, the front link 130 and the rear link 150 together with the upper thigh member 110 and the lower thigh member 120 constitute a constrained chain in which only a constant movement is allowed. The front link 130 and the rear link 150 exhibits a generally horizontal U-shaped configuration when viewed in a direction of the front side of the knee. Bodies of the respective links are in leftward and rightward symmetrical relation. Referring to FIG. 3 showing a state in which the knee is extended, FIG. 5 showing a state in which the upper thigh member 110 is more greatly projected forwardly and a bending angle of the knee is several 10 degrees, and FIG. 6 showing a state in which a bending angle of the knee is 90 degrees, it is understood that the front link 130 between the upper thigh member 110 and the lower thigh member 120 is not allowed to project forwardly exceeding the upper and lower thigh members 110, 120.

Figure 7:
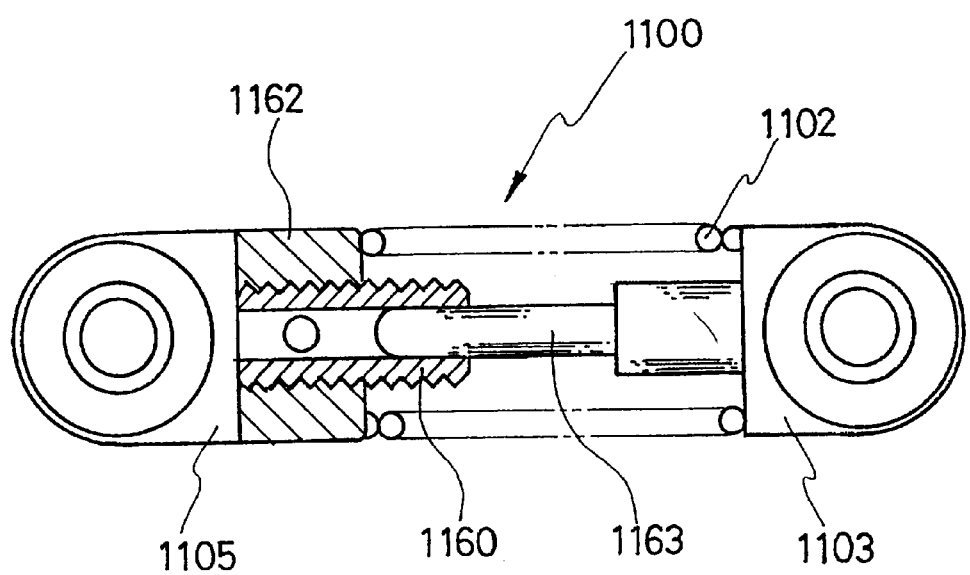
FIG. 7 is a view showing an extension auxiliary mechanism in the first embodiment, on an enlarged scale.

The extension auxiliary mechanism 1100 is bridged between the lower thigh member 120 and the rear link 150. As in the case with the bodies of the front and rear links 130, 150, mutually identical two extension auxiliary mechanisms 1100 are arranged in leftward and rightward symmetrical relation. Each of the left and right extension auxiliary mechanism 1100 includes a compression coiled spring 1102, a first spring retainer 1103 rotatably connected through a pin 1100P to the front link 130 while supporting a front end portion of the compression coiled spring 1102, and a second spring retainer 1105 rotatably connected through a pin 1100Q to the rear link 150 while supporting a rear end portion of the compression coiled spring 1102. As shown in an enlarged view of FIG. 7, the second spring retainer 1105 has an adjustment bolt 1160 integral therewith and an adjustment nut 1162 threadingly engaged with the adjustment bolt 1160. By the adjustment bolt 1160 and the adjustment nut 1162, the second spring retainer 1105 can adjust the force (i.e., initial deflecting amount) of the compression coiled spring 1102. The adjustment bolt 1160 exhibits a sleeve-like configuration. A guide rod 1163 is slidably inserted into the sleeve-like adjustment bolt 1160. The guide rod 1163 is integral with the first spring retainer 1103 on the front side. The sleeve-like bolt 1160 and the guide rod 1163 are located on an inner periphery of the compression coiled spring 1102 and adapted to guide a biasing motion of the compression coiled spring 1102.

Figure 8:
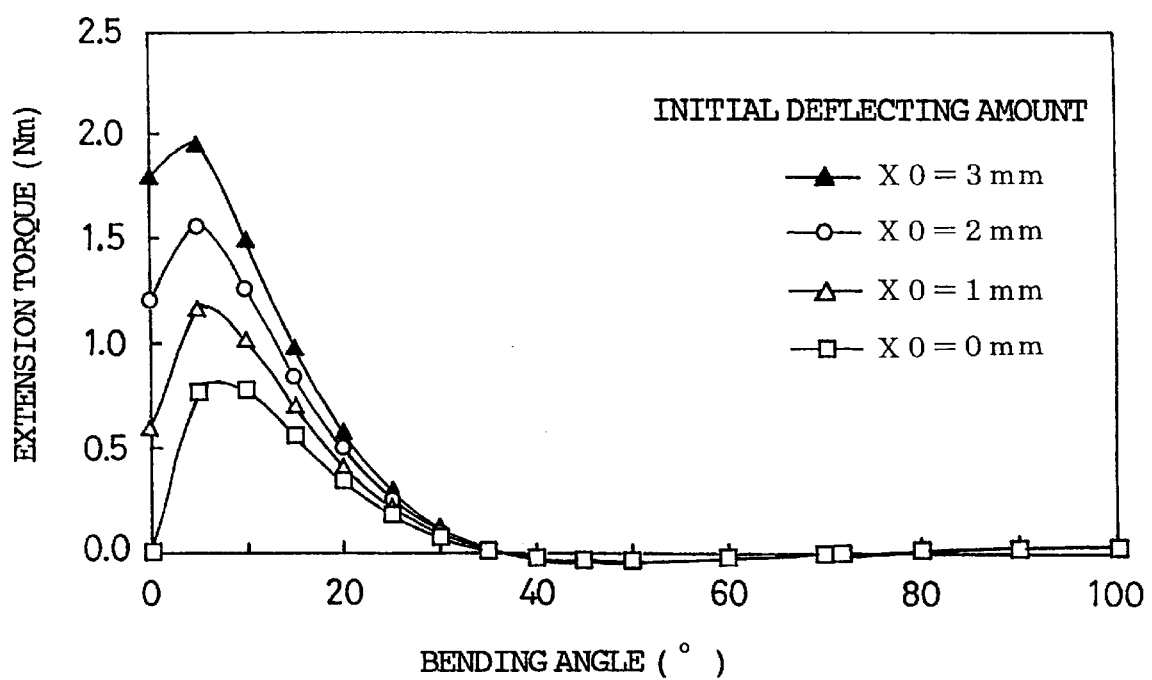
FIG. 8 is a graph showing one characteristic of the extension auxiliary mechanism in the first embodiment.
Figure 9:
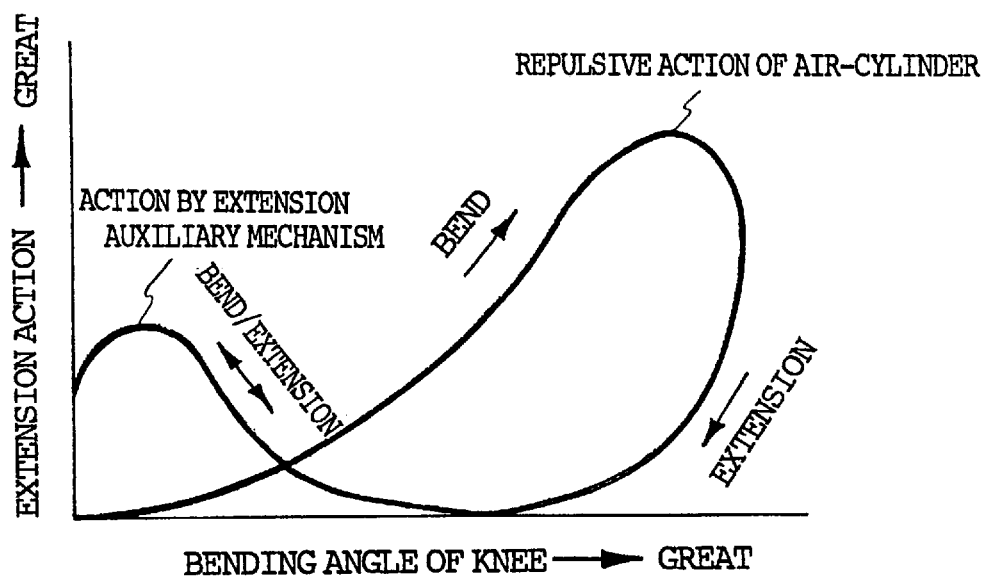
FIG. 9 is a graph showing, in combination, various actions exhibited by the extension auxiliary mechanism and the air-cylinder device.

A connecting portion (pin 1100Q) of the extension auxiliary mechanism 1100 on the rear link 150 side is located between two connecting portions 170B, 170O of the rear link 150 with respect to the upper thigh member 110 and the lower thigh member 120, but it is offset towards the front link 130 from a straight line which connects the two connecting portions 170B, 170O together. The extension auxiliary mechanism 1100 compresses and biases the compression coiled spring 1102 in accordance with bending operation of the knee to thereby increase a force F caused by the biasing of the compression coiled spring 1102. When the bending angle of the knee becomes approximately 10 degrees, a straight line (namely, axis of the compression coiled spring 1102) which connects two connecting portions 1100P, 1100Q of the extension auxiliary mechanism 1100 together is brought generally into alignment with the connecting portion 170O between the rear link 150 and the lower thigh member 120 to make the distance d approximately zero. FIG. 8 is a graph showing a relation between a bending angle of the knee and an extension torque generated by the extension auxiliary mechanism 1100. The extension auxiliary mechanism 1100 exhibits an effective extension action when the bending angle is smaller than 20 degrees, particularly in a range of from 0 to 15 degrees, but it exhibits no extension action when the bending angle is larger than 20 degrees. FIG. 9 is a graph showing a correlation between an extension action caused by the extension auxiliary mechanism 1100 and a repulsive action caused by the air-cylinder 90. As apparent from this graph, since the extension auxiliary mechanism 1100 and the air-cylinder device 90 act at mutually different ranges of bending angles of the knee, their actions are mutually independent. The upper thigh member 110 is provided with a stopper 110s having a cushioning function. Abutment of the front link 130 against the stopper 110s restricts a further extension of the knee.

Figure 10:
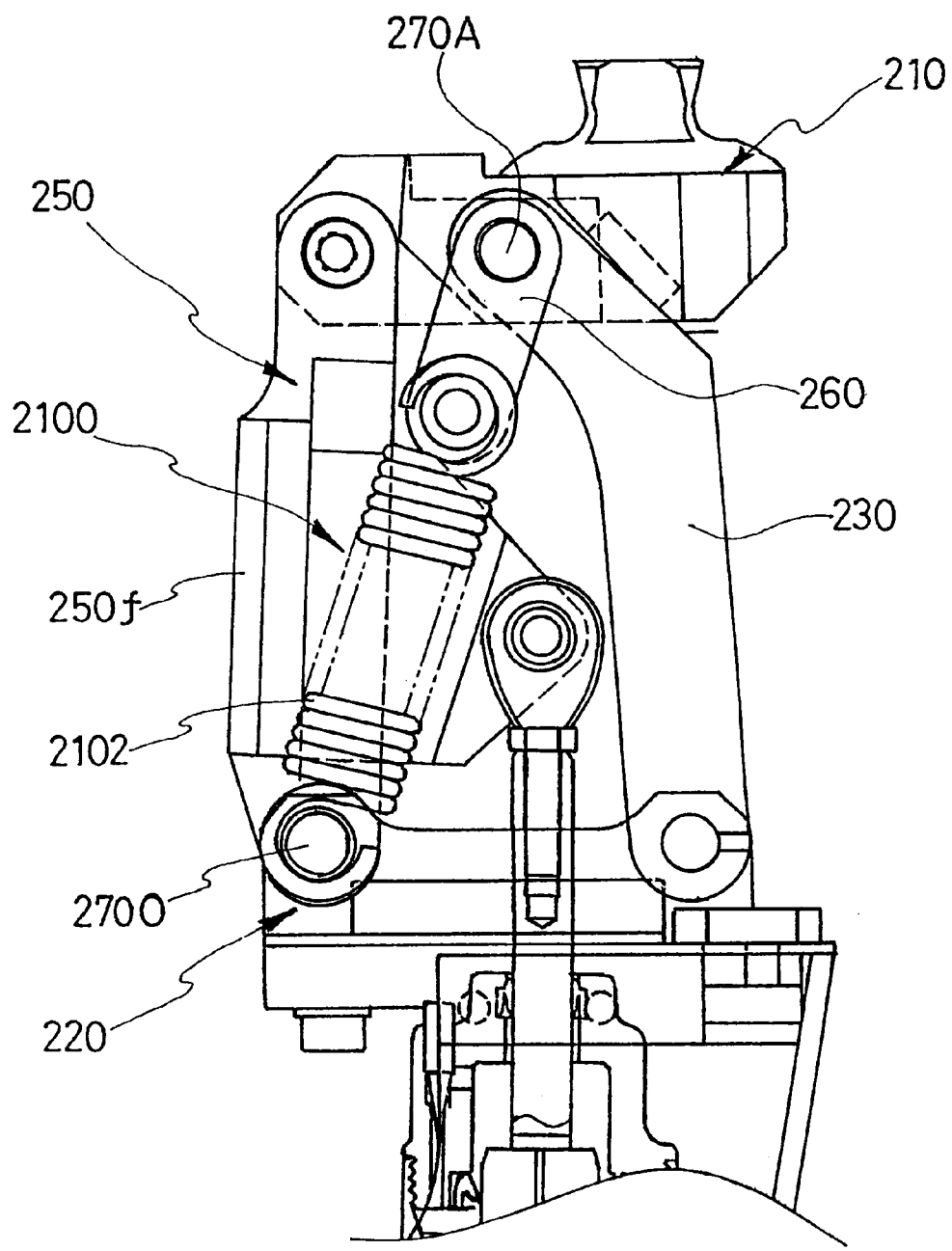
FIG. 10 is a view showing a construction of an essential portion of a thigh prosthesis according to the second embodiment of the present invention.
Figure 11:
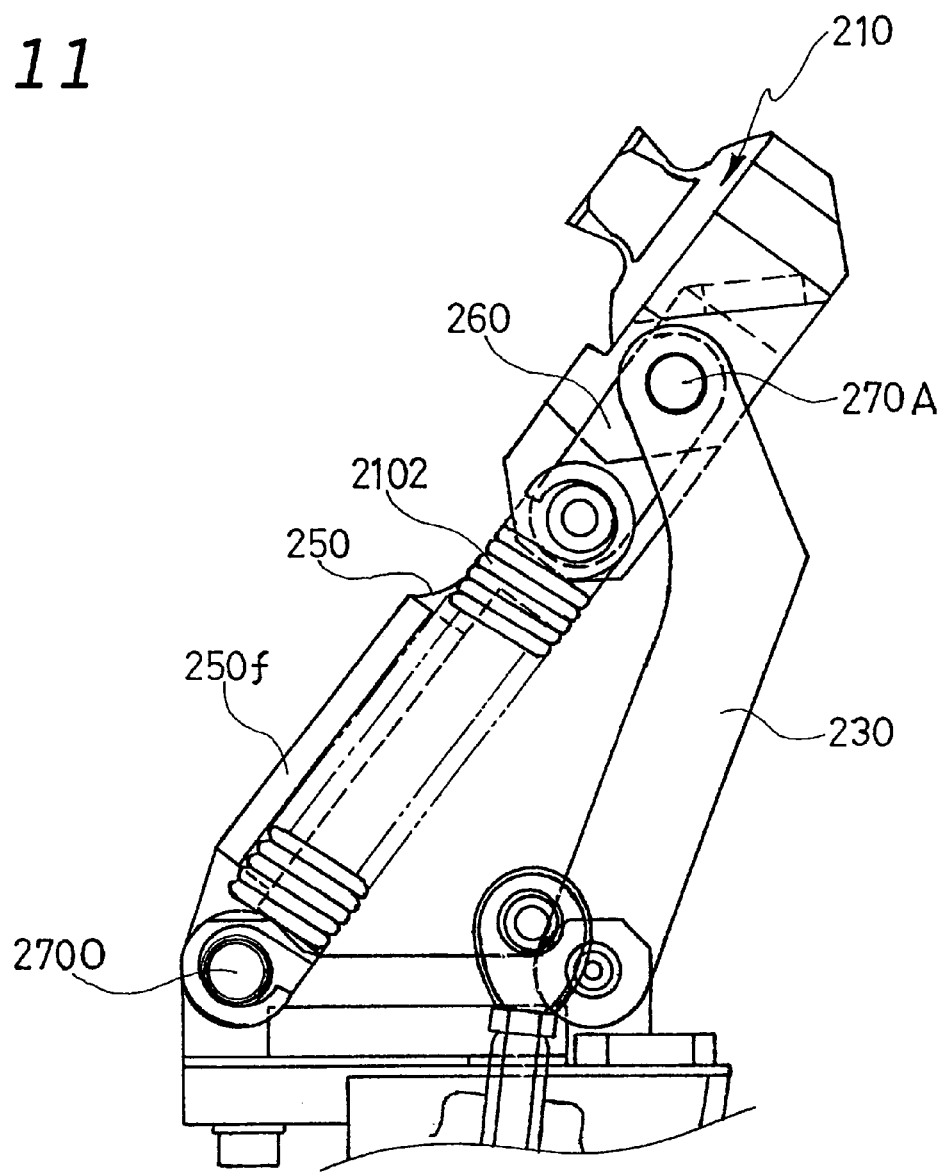
FIG. 11 is a partial view of FIG. 10, but it shows another bending state of the thigh prosthesis.
Figure 12:
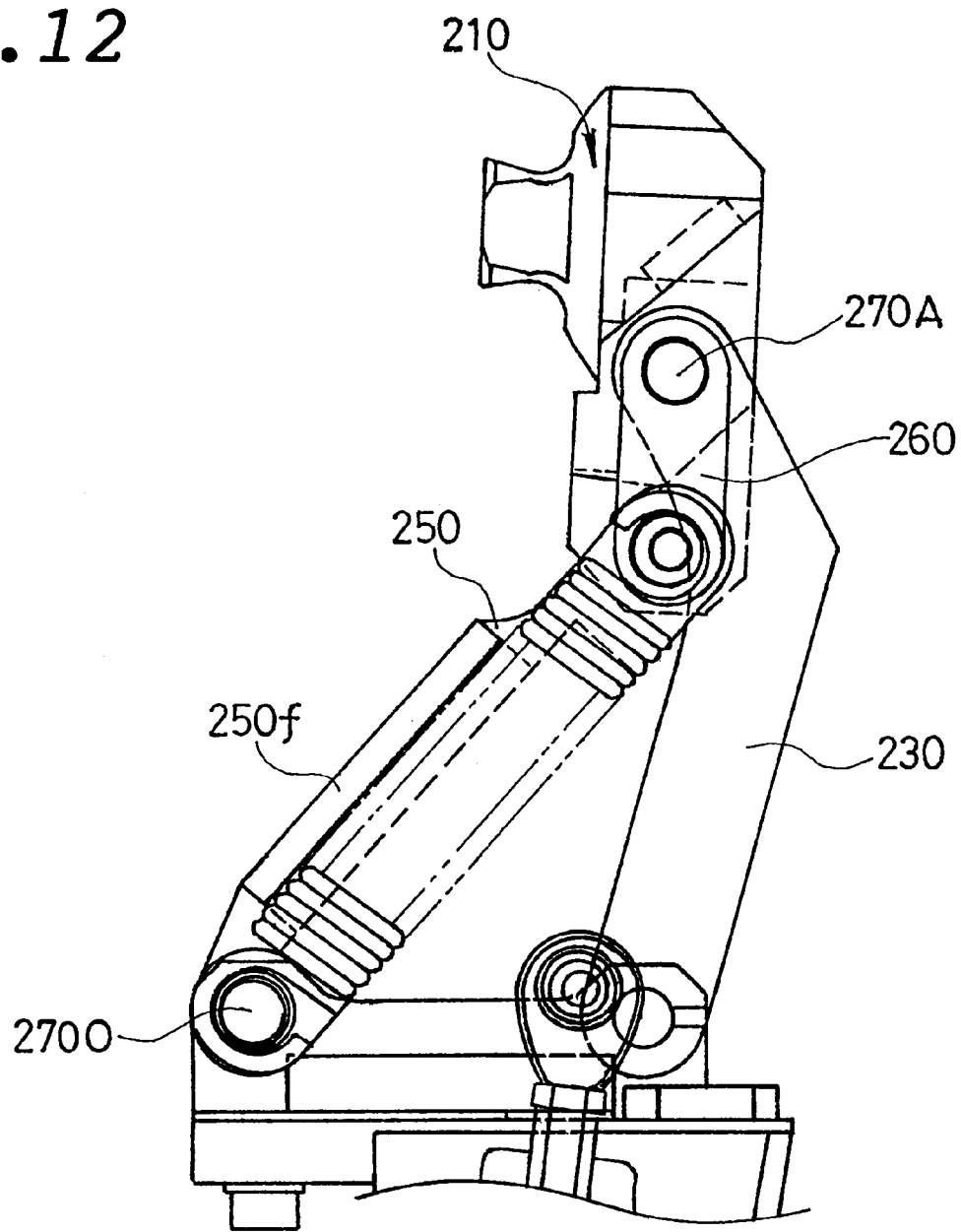
FIG. 12 is a partial view of FIG. 10 but, it shows a state in which the thigh prosthesis is bent approximately 90 degrees.

The second embodiment of the present invention will now be described with reference to FIGS. 10 to 12. FIGS. 10 to 12 show an essential portion of an upper thigh member including an extension auxiliary mechanism 2100 having a tension spring. FIG. 10 shows a state in which the knee is completely extended, FIG. 12 shows a state in which a bending angle of the knee is approximately 90 degrees, and FIG. 11 shows a state in which the knee is bent at an intermediate angle with respect to FIGS. 10 and 12.

The extension auxiliary mechanism 2100 is chiefly comprised of a tension coiled spring 2102. The extension auxiliary mechanism 2100 is connected for support between a connecting portion 270A of a front link 230 with respect to an upper thigh member 210 and a connecting portion 270O of a rear link 250 with respect to a lower thigh member 220. For connection, the extension auxiliary mechanism 2100 is connected to the front link 230 side through an auxiliary link 260. Referring again to FIGS. 10 to 12 in order, the rear link 250 includes a raised portion 250f for limiting a swinging motion of the tension coiled spring 2102 so that an axis of the tension coiled spring 2102 is brought into alignment with that of the rear link 250 at a stage where a bending angle of the knee is still small. By virtue of a provision of the auxiliary link 260, no rotational torque is generated by the extension auxiliary mechanism 2100 in a bending direction of the knee when the bending angle is increased.

What is claimed is:

1. A prosthetic leg with a knee joint, comprising an upper thigh member to which a load of a wearer is incurred through the thigh, a lower thigh member connected to said upper thigh member at the knee portion, and a knee joint including at least two front and rear links, one being located forwardly of the knee and the other being located backwardly of the knee, said two links together with said upper thigh member and said lower thigh member constituting a constrained chain, said upper thigh member and said lower thigh member being bendably connected together through said knee joint, wherein an extension auxiliary mechanism having a spring is disposed between said front link and said rear link, said extension auxiliary mechanism generates an extension torque determined by a product of a force caused by biasing of said spring and a distance from a line of action of said force to the center of rotation of said rear link, and said distance becomes approximately zero when a bending angle of the knee exceeds a predetermined angle.

2. A prosthetic leg according to claim 1, wherein said spring of said extension auxiliary mechanism is a compression spring and disposed between said upper thigh member and said lower thigh member.

3. A prosthetic leg according to claim 2, wherein said extension auxiliary mechanism includes a compression spring, a first spring retainer for supporting one end portion of said spring and rotatably connected to said lower thigh member, and a second spring retainer for supporting the other end portion of said compression spring and rotatably connected to said rear link, an axis of said compression mechanism being brought generally into alignment with a connecting portion between said rear link and said front link after the knee is bent a predetermined angle.

4. A prosthetic leg according to claim 3, wherein a connecting portion of said first spring retainer with respect to the lower thigh member is situated between two connecting portions of said front link with respect to said upper thigh member and said lower thigh member, and a connecting portion of said second spring retainer with respect to said rear link is situated between two connecting portions of said rear link with respect to said upper thigh member and said lower thigh member and offset toward said front link from a straight line which connects said two connecting portions together.

5. A prosthetic leg according to claim 2, wherein said extension auxiliary mechanism includes means for adjusting the force of said compression spring.

6. A prosthetic leg according to claim 1, wherein said upper thigh member is provided with a stopper, so that when said front link is brought into abutment with said stopper, extension of the knee is restricted.

7. A prosthetic leg according to claim 1, wherein said spring of said extension auxiliary mechanism is a tension spring, and said tension spring is supported between a connecting portion of said front link with respect to said upper thigh member and a connecting portion of said rear link with respect to said lower thigh member.

8. A prosthetic leg according to claim 7, wherein an axis of said extension auxiliary mechanism is in overlapping relation to an axis of said rear link at the predetermined angle.

9. A prosthetic leg according to claim 7, wherein said extension auxiliary mechanism is attached to said front link through an auxiliary link.

10. A prosthetic leg with a knee joint, comprising an upper thigh member to which a load of a wearer is incurred through the thigh, a lower thigh member connected to said upper thigh member at the knee portion, and a knee joint including at least two front and rear links, one being located forwardly of the knee and the other being located backwardly of the knee, said two links together with said upper thigh member and said lower thigh member constituting a constrained chain, said upper thigh member and said lower thigh member being bendably connected together through said knee joint, said prosthetic leg further comprising an extension auxiliary mechanism disposed between said front link and said rear link, said extension auxiliary mechanism generating an extension torque for extending the knee when a bending angle of the knee is smaller than a predetermined angle, and a swing phase control unit for generating a substantial acting force when a bending angle of the knee is larger than the predetermined angle.

11. A prosthetic leg according to claim 10, wherein when a relation of a bending angle of the knee with an extension torque and an action force is reviewed, said extension auxiliary mechanism exhibits a maximum value of the extension torque at a bending angle smaller than an angle in which bending of the knee becomes maximum in a swing phase, and on the other hand, said swing phase control unit exhibits a maximum value of a substantial action force at a bending angle larger than an angle in which bending angle of the knee becomes maximum in the swing phase.

12. A prosthetic leg according to claim 10, wherein said swing phase control unit is an air-cylinder device which includes a cylinder, a piston for defining two chambers in said cylinder, and a valve for controlling a flow of air between said two chambers.

13. A prosthetic leg according to claim 12, wherein an opening degree of said valve is controlled in accordance with a walking speed of the wearer.

14. A prosthetic leg according to claim 10, wherein an extension torque of said extension auxiliary mechanism is acted when a substantial action force of said swing phase control unit is ceased.

* * * * *